US012108987B2

United States Patent
Marin et al.

(10) Patent No.: US 12,108,987 B2
(45) Date of Patent: Oct. 8, 2024

(54) METHOD FOR DETERMINING A REFRACTION FEATURE OF AN EYE OF A SUBJECT, AND ASSOCIATED PORTABLE ELECTRONIC DEVICE

(71) Applicant: ESSILOR INTERNATIONAL, Charenton-le-Pont (FR)

(72) Inventors: Gildas Marin, Charenton-le-Pont (FR); Stéphane Boutinon, Charenton-le-Pont (FR)

(73) Assignee: Essilor International, Charenton-le-pont (FR)

( * ) Notice: Subject to any disclaimer, the term of this patent is extended or adjusted under 35 U.S.C. 154(b) by 632 days.

(21) Appl. No.: 17/414,536

(22) PCT Filed: Dec. 19, 2019

(86) PCT No.: PCT/EP2019/086457
§ 371 (c)(1),
(2) Date: Jun. 16, 2021

(87) PCT Pub. No.: WO2020/127832
PCT Pub. Date: Jun. 25, 2020

(65) Prior Publication Data
US 2022/0015625 A1    Jan. 20, 2022

(30) Foreign Application Priority Data
Dec. 20, 2018  (EP) ..................................... 18306774

(51) Int. Cl.
*A61B 3/103*     (2006.01)
*A61B 3/00*      (2006.01)
(Continued)

(52) U.S. Cl.
CPC ............. *A61B 3/103* (2013.01); *A61B 3/0025* (2013.01); *A61B 3/0041* (2013.01); *A61B 3/14* (2013.01); *A61B 5/6898* (2013.01)

(58) Field of Classification Search
CPC ..... A61B 3/103; A61B 3/0025; A61B 3/0041; A61B 3/14; A61B 5/6898
(Continued)

(56) References Cited

U.S. PATENT DOCUMENTS 6,616,277 B1    9/2003  Davenport
9,891,445 B1 *  2/2018  Miller .................. G02B 27/646
(Continued)

FOREIGN PATENT DOCUMENTS

CN    105011898 A    11/2015
CN    106659376 A    5/2017
(Continued)

OTHER PUBLICATIONS

Bobier and Braddick, "Eccentric Photorefraction: Optical Analysis and Empirical Measures," American Journal of Optometry and Physiological Optics, 1985, vol. 62, No. 9, pp. 614-620.
(Continued)

*Primary Examiner* — Mohammed A Hasan
(74) *Attorney, Agent, or Firm* — NIXON & VANDERHYE (57) ABSTRACT

The method includes the steps of: a) illuminating the pupil of an eye of a subject by a light source of a portable electronic device, the light source being formed by a lighted area displayed on a screen of the portable electronic device; b) acquiring a picture of the pupil of the eye of the subject by an image-capture apparatus of the portable electronic device, the picture including an image of the reflection of the light source on the retina of the eye; and c) determining a refraction feature of the eye taking into account at least a
(Continued)

geometrical feature, a positional feature or an intensity distribution of the image of the reflection. An associated portable electronic device is also described.

12 Claims, 2 Drawing Sheets

(51) Int. Cl.
*A61B 3/14* (2006.01)
*A61B 5/00* (2006.01)

(58) Field of Classification Search
USPC .......................................... 351/206
See application file for complete search history.

(56) References Cited

U.S. PATENT DOCUMENTS

| | | | |
|---|---|---|---|
| 9,968,253 B2* | 5/2018 | Lindig | A61B 3/04 |
| 2015/0313462 A1 | 11/2015 | Reis | |
| 2015/0374224 A1 | 12/2015 | Baranton | |
| 2017/0150882 A1 | 6/2017 | Lindig | |
| 2017/0164827 A1 | 6/2017 | Lindig | |
| 2018/0235456 A1 | 8/2018 | Karakaya | |
| 2018/0279872 A1 | 10/2018 | Okamoto | |
| 2019/0206093 A1* | 7/2019 | Chen | G06T 11/00 |
| 2022/0015625 A1* | 1/2022 | Marin | A61B 3/0025 |

FOREIGN PATENT DOCUMENTS

| | | | | |
|---|---|---|---|---|
| CN | 107920733 A | 4/2018 | | |
| CN | 108604020 A | 9/2018 | | |
| WO | 2013/036629 | 3/2013 | | |
| WO | WO-2013036629 A2 * | 3/2013 | ............... | A61B 3/10 |
| WO | 2016/149416 | 9/2016 | | |
| WO | 2017/070703 | 4/2017 | | |

OTHER PUBLICATIONS

Gekeler et al., "Measurement of astigmatism by automated infrared photoretinoscopy," Optometry and Vision Science, Jul. 1997, vol. 74, No. 7, pp. 472-482.
Roorda et al., "Slope-based eccentric photorefraction: theoretical analysis of different light source configurations and effects of ocular aberrations," Journal of the Optical Society of America, A, Oct. 1997, vol. 14, No. 10, pp. 2547-2556.
International Search Report for PCT/EP2019/086457 dated Feb. 6, 2020, 5 pages.
Written Opinion of the ISA for PCT/EP2019/086457 dated Feb. 6, 2020, 6 pages.
Office Action, issued in Chinese Patent Application No. 201980084120.5 dated Apr. 26, 2024.

* cited by examiner

METHOD FOR DETERMINING A REFRACTION FEATURE OF AN EYE OF A SUBJECT, AND ASSOCIATED PORTABLE ELECTRONIC DEVICE

CROSS-REFERENCE TO RELATED APPLICATIONS

This application is the U.S. national phase of International Application No. PCT/EP2019/086457 filed Dec. 19, 2019 which designated the U.S. and claims priority to EP 18306774.3 filed Dec. 20, 2018, the entire contents of each of which are hereby incorporated by reference.

BACKGROUND OF THE INVENTION

Field of the Invention

The invention relates to a method for determining a refraction feature of an eye of a subject using a measuring device comprising a portable electronic device.

Description of the Related Art

Numerous documents describe devices and methods for determining such a refraction feature.

In particular, methods of autorefraction are known for determining objective values of the refraction of a subject. These methods are complex and time-consuming. They usually imply the use of large and expensive devices that need a qualified person to be handled.

The access to these methods of autorefraction is therefore limited and a large part of the world population does not benefit from them. Moreover, these methods are not suitable for a direct online ordering of optical equipment, carried on without a visit to an eye care professional.

SUMMARY OF THE INVENTION

Therefore one object of the invention is to provide a new method for determining a refraction feature of an eye of a subject that would be simplified in that it would not require the use of specific material or the intervention of qualified persons.

The above objects are achieved according to the invention by providing a method for determining a refraction feature of an eye of a subject using a measuring device comprising a portable electronic device, said portable electronic device including:
 a light source adapted to illuminate a pupil of said eye of the subject; and
 an image-capture apparatus adapted to acquire pictures of said pupil illuminated by said light source,
 said method comprising the steps of:
 a) illuminating said pupil of the eye of the subject by means of said light source;
 b) acquiring a picture of said pupil of the eye of the subject comprising an image of the reflection of said light source on the retina of said eye of the subject;
 c) determining said refraction feature of said eye of the subject taking into account at least one of the following features of said image of the reflection of said light source:
  a geometrical feature of said image of the reflection of said light source,
  a positional feature of said image of the reflection of said light source,
  an intensity distribution within said image of the reflection of said light source;
 wherein said portable electronic device being held by the subject himself in front of his eyes,
 said step a) comprises displaying, on a screen of said portable electronic device, a lighted area forming said light source, and
 in step b) said reflection of said light is collected by said image-capture apparatus.

Such a method may be implemented by the subject himself, and carried on using only a smartphone, or a tablet computer, with no added optical components or an augmented reality display. It is therefore accessible to a wide range of population including some that are excluded from the access to existing methods.

Optional, non-limiting features of the method for virtually testing are also disclosed and claimed.

The method can also comprise the following optional, non-limiting features:
 the gaze direction of the subject and an observation direction linking optically the pupil of the eye of the subject and the entrance pupil of the image-capture apparatus form an angle of less than 15 degrees or less than 5 degrees, or less than 1 degrees;
 in step b), the subject directs his gaze towards an entrance pupil of said image-capture apparatus or towards said light source or toward a visual target;
 the method comprises the step of synchronizing the image-capture with the display of said lighted area;
 steps a) and b) are repeated in order to capture said plurality of pictures, and in each of the repeated steps a), the relative position of the image-capture apparatus and the eye of the subject is modified while the lighted area remains centered at a same predetermined distance from the center of the entrance pupil of the image-capture apparatus;
 in each of the repeated steps a), a dimension of said lighted area is varied;
 in step c), said refraction feature of said eye of the subject is determined taking into account the relative position of the light source and the pupil of the eye of the subject during the acquisition of each picture;
 in step b), the subject wearing a corrective ophthalmic lens in front of his eye and in step c), the optical features of this corrective ophthalmic lens is taken into account for determining the refraction feature of the eye;
 in a calibration step, data relative to the position of the electronic device in space is acquired by said position determination module while the electronic device is placed against the head of the subject;
 said portable electronic device comprises a smartphone, and/or an augmented reality display and/or a device having said image-capture apparatus with an effective optical axis that crosses the display screen.

The above mentioned object is also achieved according to the invention by providing a portable electronic device. The optional features of the method mentioned above can also be applied to this portable electronic device.

BRIEF DESCRIPTION OF THE DRAWINGS

The description which follows with reference to the appended drawings, which are given by way of non-limiting examples, will make it easy to understand the essence of the invention and how it can be achieved.

In the appended drawings.

DESCRIPTION OF THE PREFERRED EMBODIMENTS

Figure 1:
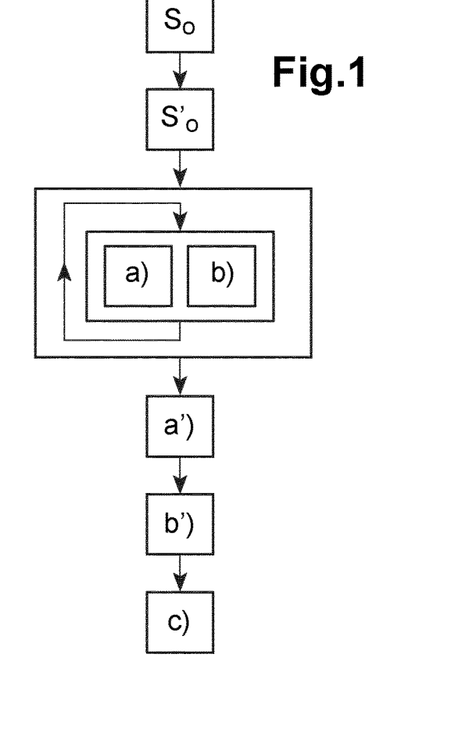
FIG. 1 is a schematic representation of the main steps of a method, according to the invention, for determining a refraction feature of an eye of a subject.

FIG. 1 represents the main steps of a method that enables to determine a refraction feature of an eye of a subject, such as a spherical power of a refractive error of this eye, using a portable electronic device 1, like a mobile phone or a tablet computer.

This portable electronic device 1; 1' comprises:
a light source adapted to illuminate a pupil 30 of the eye 3 of the subject 2, and
an image-capture apparatus 10 adapted to acquire pictures of said pupil 30 illuminated by said light source.

The method for determining the refractive feature of the eye 3 of the subject 2 comprises the steps of:
a) illuminating said pupil 30 of the eye 3 of the subject 2 by means of the light source of the portable electronic device 1; 1', said light source 12A, 12B, 12C being formed by a lighted area displayed on a screen 11 of the portable electronic device 1; 1' (FIGS. 4A to 4C);
b) acquiring a picture of said pupil 30 of the eye 3 of the subject by means of the image-capture apparatus 10 of the portable electronic device 1; 1', said picture comprising an image of the reflection 31 of said light source 12A, 12B, 12C on the retina of said eye 3 of the subject (FIG. 3); and
c) determining said refraction feature of said eye 3 of the subject taking into account at least one of the following features of said image of the reflection 31 of said light source 12A, 12B, 12C:
a geometrical feature, such as a size $\underline{s}$ of said image of the reflection 31 of said light source,
a positional feature, such as an orientation, of said image of the reflection 31 of said light source,
a light distribution within said image of the reflection 31 of said light source, such as an intensity profile of said image.

In the exemplary embodiments described here, in step c), said refraction feature of said eye 3 of the subject is determined more specifically by taking into account at least one of the following features of said image of the reflection 31 of said light source 12A, 12B, 12C:
a size $\underline{s}$ of said image of the reflection 31 of said light source,
an orientation of said image of the reflection 31 of said light source,
an intensity profile of said image of the reflection 31 of said light source.

In this method, the determination of the refraction feature of the eye 3 of the subject is based on the technique of eccentric photorefraction, a type of retinoscopy technique, as described for instance in the article "Eccentric Photorefraction: Optical Analysis and Empirical Measures" by W. R. Bobier and O. J. Braddick (American Journal of Optometry and Physiological Optics, 1985, vol. 62, No. 9, pp. 614-620).

The refraction features that can be determined using this technique comprise: the spherical power of a refractive error of the eye to characterize, a cylindrical power of this refractive error, and an orientation of the axis of the corresponding cylinder.

Figure 4A:
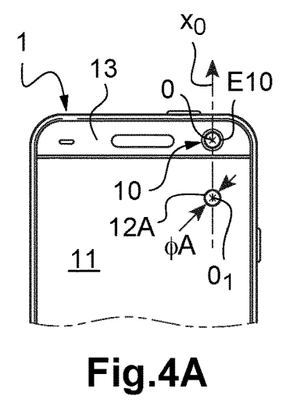
FIGS. 4A to 4C are schematic front views of the portable electronic device of FIG. 2, showing a lighted area displayed on a screen of this portable electronic device.

According to this technique, the light source 12A, 12B, 12C that illuminates the pupil 30 of the eye 3 is shifted laterally with respect to the entrance pupil E10 of the image-capture apparatus 10 (see FIG. 4A, for instance). In the embodiments described here, this light source 12A, 12B, 12C has an emitting surface that forms a small spot.

Figure 3:
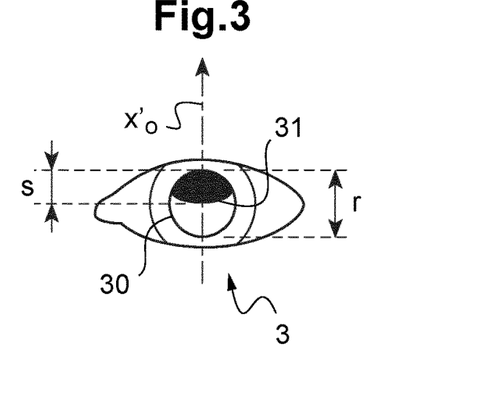
FIG. 3 is a schematic representation of an eye of the subject of FIG. 2, as it is seen from the position of an image-capture apparatus.

When the eye 3 of the subject is ametropic, in a picture of this eye 3 acquired by the image-capture apparatus 10, an image of the reflection 31, on the retina of the eye 3, of said light source 12A, 12B, 12C, occupies a portion only of the image of the pupil 30 of this eye, this portion being in the shape of a crescent (FIG. 3). More precisely, this retinal reflection 31 is bounded by two curved arcs that intersect each other to form two sharp ends of the crescent.

A size $\underline{s}$ of the reflection 31 thus detected provides information regarding a value of the ametropia of the eye 3.

Here, the size $\underline{s}$ of said reflection 31 designates a width of this reflection, in a direction $x'_o$ parallel to a measurement axis $x_o$ that passes through a center O of the entrance pupil E10 of the image-capture apparatus 10, and through the point O1 on which the light source 12A, 12B, 12C is centered. In other words, the size $\underline{s}$ is the extent of said reflection 31, along said direction $x'_o$. The size $\underline{s}$ is the width of this reflection 31 in real space, in the plane of the pupil 30 of the eye.

The size $\underline{s}$ of the reflection 31, in real space, can be determined from a dimension $s_I$ of the image of this reflection, expressed as a number of pixels, for instance, measured in the picture of the eye 3 captured by the image-capture apparatus 10. The dimension $s_I$ of the image of the reflection 31, measured in the picture of the eye 3 captured by the image-capture apparatus 10, can be determined, for instance, as the full width at half-maximum of an intensity peak of an intensity profile of said image.

It is then known that a value of the ametropia of the eye 3, equal to a spherical power of a refractive error of this eye 3, can be determined on the basis of:
the above-mentioned size $\underline{s}$ of the crescent-like reflection 31, on the retina of the eye, of the light source 12A, 12B, 12C,
a diameter $\underline{r}$ of said pupil 30,
a distance $d_{cam}$ between the entrance pupil E10 of the image capture apparatus 10 and the pupil 30 of the eye 3 of the subject 2, and of
an eccentricity e between the light source 12A, 12B, 12C and the entrance pupil E10 of the image capture apparatus 10.

This eccentricity e is representative of a side shift between the light source 12A, 12B, 12C and the entrance pupil E10 of the image capture apparatus 10.

More precisely, the eccentricity e is determined as the smallest, minimal) distance between:
- the entrance pupil E10 of the image capture apparatus 10, and
- the light source 12A, 12B, 12C.

So, the eccentricity e is determined as the distance e1 between:
- the point of the entrance pupil E10 which is the closest to the light source 12A, 12B, 12C, and
- the point of the light source 12A, 12B, 12C which is the closest to the entrance pupil E10.

Regarding the sign of the ametropia, negative for myopia and positive for hypermetropia, it can be determined on the basis of the position of said reflection 31, relative to an observation direction $z_o$ that links optically the pupil 30 of the eye 3 to the entrance pupil E10 of the image-capture apparatus.

When this reflection 31 is located on the same side of the observation direction $z_o$ than the light source, the ametropia is negative. In such a case, for instance, both the reflection 31 and light source 12A, 12B, 12C could be located below the observation direction $z_o$, or on a right side of the observation direction $z_o$. On the contrary, when this reflection 31 is located on the opposite side of the observation direction $z_o$ than the light source, the ametropia is positive.

Figure 5:
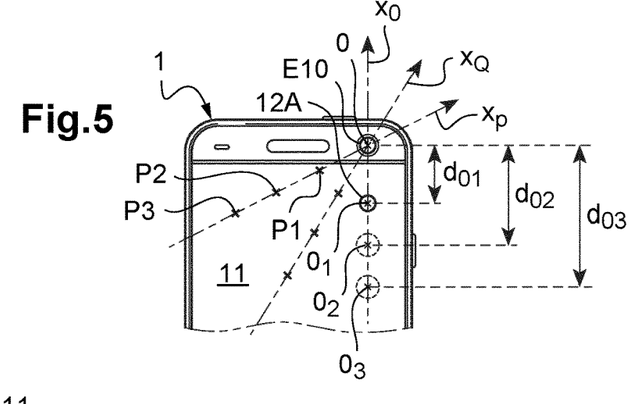
FIG. 5 is a schematic front view of the portable electronic device of FIG. 2, showing various positions of the lighted area displayed on the screen of this portable electronic device.

Regarding astigmatism features, comprising the cylindrical power of the refraction error of the eye 3, and the orientation of the axis of the corresponding cylinder, they can be determined by acquiring several pictures of the eye 3 of the subject 2, for a respective plurality of measurement axis, $x_o$, $x_P$, $x_Q$ having different respective orientations relative to the face/eye of the subject (FIG. 5). As explained above, each of these measurement axis $x_o$, $X_P$, $X_Q$ identifies the direction that passes through the center O of the entrance pupil E10 of the image-capture apparatus 10, and through the point O1, P1, Q1 on which is centered the light source 12A, 12B, 12C during the relevant picture acquisition.

The size s of the reflection 31 can thus be determined for each of these orientations, and hence, for different meridians of the eye 3.

In addition, for each of these orientations, that is for each of these measurement axis $x_o$, $x_P$, $x_Q$, the shape of the crescent-like image of said reflection 31 can be exploited to determine an orientation, that is, an angular position of this reflection 31, with respect to the relevant measurement axis $x_o$, $x_P$, $x_Q$. This orientation corresponds here to a tilt angle between the axis of said crescent and a direction perpendicular to the relevant measurement axis $x_o$, $x_P$, $x_Q$. The axis of the crescent is the axis that passes through the two sharp ends of the crescent mentioned above.

The cylindrical power of the refraction error of the eye 3, and the orientation of the axis of the corresponding cylinder can then be determined, from this set of values of the size s and of the tilt angle of the reflection 31, determined for the respective plurality of orientations of said measurement axis $x_o$, $x_P$, $x_Q$. This determination can be realized as explained in the article "Measurement of astigmatism by automated infrared photoretinoscopy", by Gekeler F., Schaeffel F., Howland H C. and Wattam-Bell J. (Optometry and Vision Science, July 1997, 74(7), pages 472-82), for instance.

The refraction features of the eye of the subject can also be determined on the basis of an intensity profile of the reflection 31 of the light source on the retina of the eye 3 of the subject, instead of being determined on the basis of the sizes of the retinal reflection 31.

In this case, the lighted area, displayed on the screen 11 to form said light source, comprises preferably several small lighted dots, instead of a single spot-like area, as in the case of FIG. 4A. These different dots are displayed on the screen at various positions, in order to have various eccentricities with respect to the entrance pupil of the image-capture apparatus. These dots can be positioned on the screen in order to form an array of dots, for instance. This feature improves the linearity of slope of the intensity profile of the retinal reflection 31.

This intensity profile of the retinal reflection 31 is a cross section of the intensity of said reflection 31, across a meridian of the pupil 31, for instance across the meridian of the pupil parallel to said measurement axis. In other words, this intensity profile is an ensemble of values representative of the variation of the intensity, that is to say representative of the variation of the luminous power, or of the variation of the luminous power per area, within the reflection 31, as a function of a position across said meridian of the pupil.

The determination of the refraction features of the eye of the subject, from this intensity profile can be achieved according to the following article, for instance: "Slope-based eccentric photorefraction: theoretical analysis of different light source configurations and effects of ocular aberrations" by A. Roorda, M. Campbell and W. Bobier (Journal of the Optical Society of America, A, Vol. 14, No. 10, October 1997, pp 2547-2556).

In the present method, the refraction features of the eye of the subject could also be determined both:
- on the basis of the size/orientation of the retinal reflection 31, and
- on the basis of the intensity profile of the retinal reflection 31.

In this case, the values of the refraction features determined from said size/orientation can, for instance, be averaged with those deduced from the intensity profile to obtain estimations of these refraction features having an improved accuracy/reliability.

The technique of eccentric photorefraction, whose principle has been recalled above, is usually implemented using dedicated devices that are expensive and designed to be handled almost exclusively by eye care professionals.

On the contrary, the method for determining a refraction feature of the eye 3 of the subject 2, that has been defined above, can be implemented by the subject 2 himself, and carried on using only a smartphone or a tablet computer with no added optical components, or using an augmented reality display. It is therefore accessible to a wide range of population including some that are excluded from the access to existing methods In addition, forming said light source by displaying a lighted area on the screen of the portable electronic device provides a lot of flexibility, enabling to easily change the characteristics of the light source, like its size, position and/or shape in the course of a sequence of measurements.

Forming said light source by displaying a lighted area on this screen also enables to display instructions and/or feed-back pictures that help the subject to achieve a proper ametropia determination, in an area that is close to a gaze direction appropriate for eccentric photorefraction. Thus, the subject can see these instructions and/or feed-back pictures without deviating his gaze direction from a direction appropriate for eccentric photorefraction.

In a first embodiment, the portable electronic device 1, configured to implement the method presented above, is a standard, general purpose smartphone or tablet computer (represented on FIG. 2), without any added component except from a dedicated computer program whose execution causes to execute the steps of said method.

Figure 6:
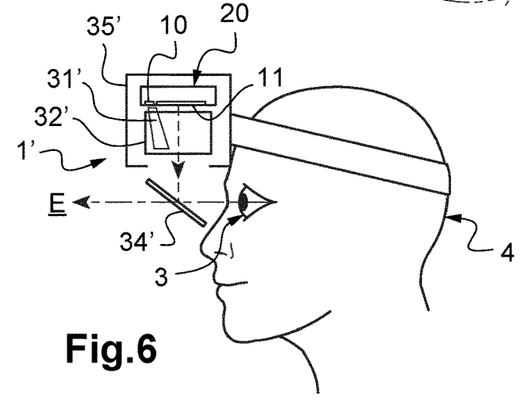
FIG. 6 is a schematic side view of a subject, holding a portable electronic device according to another embodiment.
Figure 7:
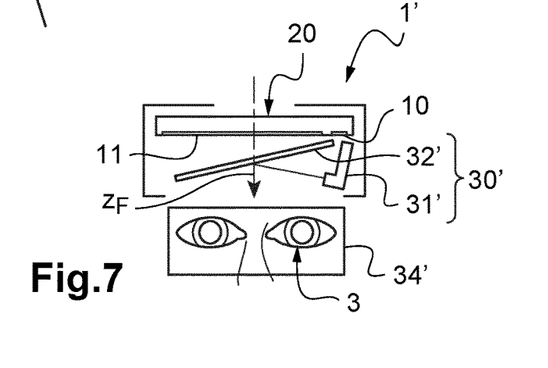
FIG. 7 is a schematic front view of the portable electronic device of FIG. 6.

In a second embodiment, the portable electronic device, configured to implement the method presented above, is an augmented reality device (as represented schematically on FIGS. 6 and 7), or a virtual reality device.

These two embodiments of the portable electronic device 1; 1' will be presented first.

Then, the main characteristics of the method implemented by this device will be described in detail.

Features improving the determination accuracy of the eye ametropia, particularly when the screen brightness or lighting capabilities are limited, will then be described, in a section relative to lighting conditions management.

First Embodiment of the Portable Electronic Device

Figure 2:
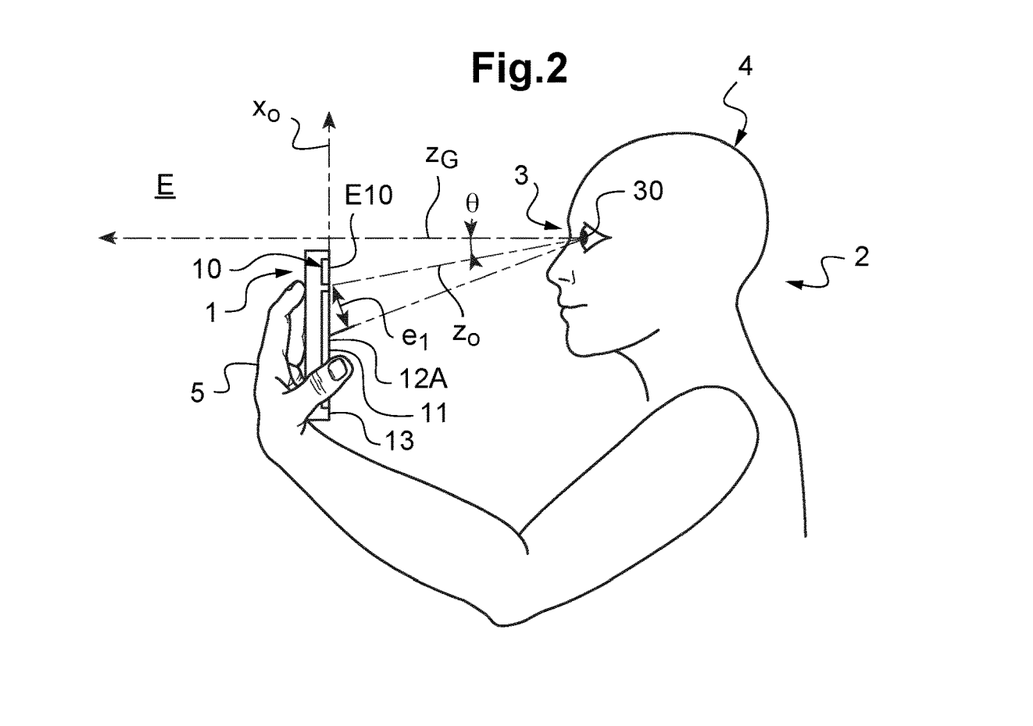
FIG. 2 is a schematic representation of a subject, holding a portable electronic device programmed to execute the method of FIG. 1.

As already mentioned, the portable electronic device 1 according to this first embodiment is a smartphone, or a tablet computer (as represented on FIG. 2, it is a smartphone).

It is small, thin and light enough so that it can be hand-held, preferably with one hand 5 only. It has the shape of a flat and thin slab.

The screen 11 of the portable electronic device 1, for instance a back-lighted LCD screen ("Liquid Crystal Display" screen), or an OLED screen ("Organic Light Emitting Diode" screen), occupies more than half of a front face 13 of the portable electronic device 1.

The image-capture apparatus 10 is located on the same face 13 as the screen 11. Its field of view, and the light emitted by the screen 11 extend on the same side of the portable electronic device 1. The image capture apparatus 10 is a small, general purpose digital camera, optimized for taking pictures of a face of a subject, of documents approximately the size of an A4 or B4 page, or of global scenes comprising elements ranging from approximately 0.3 meter to infinity. The camera does not protrude significantly, or even does not protrude at all from the front face 13 of the device. The entrance pupil E10 of the image-capture apparatus 10 is located in the vicinity of the entrance face of the lens of the image-capture apparatus 10 (as represented schematically on FIG. 4A, for instance), and has a diameter close to the diameter of said entrance face.

Here, the portable electronic device 1 comprises an optional communication module (not represented on the figures), that enables to exchange data between the portable electronic device 1 and a remote computer or server through a communication network like the internet.

The portable electronic device 1 comprises also a position determination module (not represented on the figures), suitable to deliver data relative to a position and/or orientation of the portable electronic device. This module comprises an inertial unit, that comprises an accelerometer, for instance, a three-axis accelerometer, and/or a gyroscope. This module may also comprise a magnetometer, or a digital compass, able to determine an orientation of the portable electronic device relative to a direction of the local magnetic field at the position of the portable electronic device.

The portable electronic device 1 comprises also a control unit (not represented on the figures), comprising at least a processor and a memory.

Remarkably, except from the dedicated computer program, like a computer application, sometimes called "applet", stored in said memory, whose execution by the processor causes to execute the steps of the above-mentioned method, the portable electronic device 1 has no additional features or components, compared to a standard, general purpose, stand-alone smartphone or tablet computer designed mainly for communication, that is to telephone, to participate to a videoconference or to access webpages.

In particular, the portable electronic device 1 does not comprise any additional, specific optical component that would be placed in front of the image-capture apparatus 10, or in front of the screen 11.

Thus, when step a) of said method is executed, by means of this portable electronic device 1, the light emitted by the light source 12A, 12B, 12C formed by displaying a lighted area on the screen 11, that illuminates the pupil 30 of the eye 3, reaches this eye 3 directly, without interacting with any other optical component of said portable electronic device 1. More precisely, this light reaches the eye 3 of the subject 2 without interacting with any optical component, except from, optionally, a corrective ophthalmic lens or a contact lens worn by the subject 2.

Similarly, when step b) of said method is executed thanks to this portable electronic device 1, the reflection 31 of the above-mentioned light, on the retina of the subject 2, is collected directly by the image-capture apparatus 10, without interacting with any other optical component of said portable electronic device 1. So, no optical component, except from, optionally, a corrective ophthalmic lens or a contact lens worn by the subject 2, stands optically between the eye 3 of the subject 2 and the portable electronic device 1, when step b) is executed thanks to this portable electronic device 1.

Second Embodiment of the Portable Electronic Device

As already mentioned, in this second embodiment, the portable electronic device is an augmented reality device or a virtual reality device. As represented on FIGS. 6 and 7, the portable electronic device 1' is an augmented reality device, that is a device enabling the subject 2 to see his environment E directly, and at the same time, to see information, pictures or light sources displayed by means of a screen, visually superimposed to this environment E.

The portable electronic device 1' comprises:
 a screen, similar, and even identical, here, to the screen 11 of the first embodiment,
 an image-capture apparatus, similar, and even identical, here, to the image-capture apparatus 10 of the first embodiment, and
 a headset structure 35', configured to hold said screen 11 and image-capture apparatus 10, and to be worn on the head 4 of the subject 2.

As this screen and the image-capture apparatus are identical to those of the first embodiment, they are labeled by the same reference numbers, 10 and 11 respectively.

In this example, the portable electronic device 1' comprises a smartphone 20 or any device able to provide an image to the subject, identical or similar to the smartphone of the first embodiment, including a screen 11 and image-capture apparatus 10 such as those described above.

The portable electronic device 1' comprises a first optical combiner 30', optically coupled to the image-capture apparatus 10 in order to shift and/or deviate its optical axis. The field of view of the ensemble comprising the image-capture apparatus 10 and the first optical combiner 30' is centered on an optical axis called $z_F$. The first optical combiner 30' is configured so that this optical axis $z_F$ extends in front of the screen 11, crossing said screen 11, while the optical axis of the bare image-capture apparatus 10 passes aside of the screen 11, without crossing it.

The first optical combiner 30' may comprise a semi-reflecting mirror and/or an optical deviating system, like a light-guide. In the example represented on FIGS. 6 and 7, it comprises:

a semi-reflecting mirror 32', interposed optically between the eye 3 of the subject 2 and the screen 11, for instance placed in front of the screen 11 in an inclined manner with respect to the screen 11, and an optical deviating system 31', that deviates the field of view of the image-capture apparatus 10 towards the semi-reflecting mirror 32', so that, after reflection on this semi-reflecting mirror 32', the sifted optical axis $z_F$ defined above crosses the screen 11. The optical deviating system 31' may be realized by mean of an optical guide, or by mean of a right angle prism with a 90 degrees deviation.

The portable electronic device 1' also comprises a second optical combiner 34', configured to superimpose a virtual image of the screen 11 onto the environment E of the subject 2. The second optical combiner 34' may comprise a semi-reflecting mirror disposed to reflect the light emitted by the screen 11 towards the eye 3 of the subject 2. This semi-reflecting mirror may be a bare transparent plate, optionally slightly curved to increase the optical distance between the screen 11 and the eye 3 of the subject, that is, to project said virtual image ahead of the eye 3 of the subject, far from it, for instance 1 or 2 meters ahead of his eye 3, or even infinitely far from it, from an optical point of view.

The portable electronic device 1' according to this second embodiment requires a few more components than the portable electronic device 1 of the first embodiment: in addition to the smartphone 20, it requires the headset structure 35', that integrates the optical components 30', 34' described above. However, such a headset structure 35' is nowadays a general public, widely spread product, far less expensive than a dedicated professional reflectometry apparatus.

Thanks to the first optical combiner 30', the portable electronic device according to this second embodiment enables to measure ametropia, using eccentric photorefraction, for very small values of eccentricity. Indeed, as the optical axis $z_F$ crosses the screen 11, very small lateral shifts, between this axis and the light source formed by displaying an illuminated area on the screen 11, can be obtained. Realizing such measurements for small values of eccentricity enables to measure accurately small values of ametropia.

In addition, in this second embodiment, the relative positions of the eye 3 of the subject, with respect to the light source displayed on the screen 11, and with respect to the image-capture apparatus 10, are very stable, and can thus be precisely determined prior or during the execution of the method for determining a refraction feature of an eye of the subject.

The subject also spontaneously focus his eye 3 on elements located far away from him, as he always sees his far-sighted environment, as the screen 11 of the portable electronic device is merely superimposed, in a semi-transparent manner, to his environment, and thus does not obstruct the field of view of the subject 2.

Alternatively, the portable electronic device according to this second embodiment could be realized as a virtual reality device. In this case, instead of seeing directly this environment, the subject sees a picture of this environment displayed, usually with additional features, on the screen of device, placed in front of his eyes. The picture of his environment is captured, for instance, by means of a front camera having a field of view extending opposite the screen.

Instead of being realized by means of the above-mentioned smartphone, the portable electronic device according to this second embodiment could be realized by means of an image-capture apparatus that is not integrated into the electronic device comprising said screen. Moreover, the screen and image-capture apparatus could be suitable for, respectively, emitting and capturing infra-red light, instead of visible light, so that the eye of the subject is not disturbed during this ametropia measurement, its pupil remaining widely opened.

Detailed Presentation of the Method for Determining a Refraction Feature of the Eye of the Subject During the execution of the method, the portable electronic device 1; 1' is hold by the subject 2, either in his hand 5, in his hands, or on his head 4.

When hold in his hand 5, or hands, the portable electronic device 1 is hold approximately at an arm's length from the head 4 of the subject, at a distance comprised between 0.2 and 1 meter.

Except from features (described in more detail below) related to:

position and/or distance calibration based on data delivered by the position determination module of the portable electronic device 1, modifications of the position/orientation of the image-capture apparatus 10 relative to the eye 3 of the subject, and to distance conversions, the method can be implemented in the same way by means of the first embodiment of portable electronic device 1, and by means of the second embodiment of the portable electronic device 1'.

The method is described below in the case of a determination of the refractive features of the eye based on the size and orientation of the retinal reflection 31. However, these refractive features could also be determined on the basis of one or several intensity profiles of said reflection, as mentioned above.

This method comprises, prior to the steps a) and b), a preliminary calibration step So (FIG. 1).

During this calibration step, the portable electronic device 1 determines an optical distance d between the pupil 30 to be illuminated, and the entrance pupil E10 of the image-capture apparatus 10.

In the case in which the method is executed by the portable electronic device 1 according to the first embodiment, this optical distance d is the geometrical distance $d_{cam}$ between the pupil 30 to be illuminated and the entrance pupil E10 of the image-capture apparatus 10 (FIG. 2), except if a mirror is interposed on the optical path linking the screen 11 to the eye 3 of the subject 2.

In the case in which the method is executed by the portable electronic device 1' according to the second embodiment, this optical distance d is the geometrical distance between:

the pupil of the eye 3, and the image-capture apparatus as it is seen from the subject point of view.

In other words, this optical distance d is the geometrical distance $d'_{cam}$ between the pupil of the eye 3 and a virtual image of the entrance pupil of the image-capture apparatus 10 formed by the optical components 30', 34' interposed optically between the eye 3 and the image-capture apparatus 10.

The optical distance d between the pupil 30 to be illuminated, and the entrance pupil of the image-capture apparatus 10 can be determined by scaling a picture of the subject's face, eyes or eye acquired by the image-capture apparatus 10, in position of use, that is, for instance, hold at an arm-length distance from the eye 3.

To this end, the subject may be incited, by a message displayed on the screen 11, or by an audible message, to hold a predetermined object, like a credit card, close to his eye. The above-mentioned picture is then acquired by the image-capture apparatus 10. The predetermined object has a known size, for instance a known width, whose value is stored in the memory of the portable electronic device.

From the size of that object, measured in the acquired picture, and thus expressed as a number of pixels, the portable electronic device 1; 1' determines the optical distance d between the pupil 30 and the entrance pupil E10 of the image-capture apparatus 10. To this end, the portable electronic device 1; 1' may use a calibration curve or look-out table relating the size of such an object, measured in an acquired picture, to said distance d, this calibration curve or look-out table being stored in the memory of the portable electronic device 1; 1'.

The determination of the optical distance d, by scaling a picture of the subject's face, eyes or eye acquired by the image-capture apparatus 10, could also be carried on by:
  identifying, in said picture, at least two remarkable points of the subject's face, and by
  determining said distance d as a function of at least a distance, expressed as a number of pixels, in the captured image, between these two remarkable points.

These remarkable points are points of the face that can be easily identified and precisely and located by image analysis. One of these points can be located, for instance, at the medial or lateral commissure, or at the center of the pupil of one of the eyes of the subject.

A reference distance between the two identified remarkable points is stored in the memory of the portable electronic device, and the portable electronic device is configured to:
  compare the distance, in the captured image, between the two identified remarkable points, to this reference distance, and to
  determine the optical distance d on the basis of the result of this comparison.

The picture scaling described above is also used to determine a conversion coefficient C, that relates the size of an element of the eye of the subject, in an image captured by the image-capture apparatus 10, expressed as a number of pixels, to the actual size of this element, in real space, expressed for instance in millimeters. This conversion coefficient C is employed, in step c), to determine the diameter r of the pupil 30 of the eye 3 and the size $\underline{s}$ of the retinal reflection 31, from the picture or form the pictures of eye 3 acquired in step b).

Alternatively, In the case in which the method is executed by the portable electronic device 1 according to the first embodiment, the optical distance d, that is then equal to the geometrical distance $d_{cam}$ between the pupil 30 of the eye 3 and the entrance pupil E10 of the image-capture apparatus 10, can be determined on the basis of data relative to a position of the portable electronic device 1 in space, acquired by the position determination module of the portable electronic device 1.

To this end, the subject 2 may be incited, by a message displayed on the screen 11, or by an audible message:
  to place the portable electronic device 1 against his head 4, for instance against his forehead, and then
  to place the portable electronic device 1 at his position of use for the execution of the method, approximately at an arm-length distance in front of him.

An acceleration signal delivered by the inertial unit is then integrated over time, between these two situations, thus providing data representative of the distance $d_{cam}$ between the pupil 30 of the eye 3, and the image-capture apparatus 10, at its position of use.

In the example represented on FIG. 1, the calibration step So is executed prior to steps a), b). However, alternatively, the calibration step So could be executed after steps a) and b), or in the course of the execution of a sequence of several successive executions of steps a) and b).

This method also comprises, prior to the steps a) and b), a step for giving measurement instructions to the subject, S'o (FIG. 1).

During this step, the subject 2 is incited, by a message displayed on the screen 11, or by an audible message, to look at a particular point, or in a particular direction.

More precisely, during this step S'o, the subject 2 is incited to direct his gaze towards:
  the entrance pupil E10 of said image-capture apparatus 10, or
  towards said light source 12A, 12B, 12C, or
  towards a visual target 6
  during the execution of the method.

The visual target 6 is preferably located in a direction close to the direction linking optically the eye 3 of the subject to the light source or entrance pupil E10.

Thanks to this message, the subject 2 directs his gaze towards one of these elements during the execution of the method.

So, thanks to the above-mentioned message, during the execution of the method:
  the gaze direction $z_G$ of the subject 2 and
  the observation direction $z_o$ linking optically the pupil 30 of the eye 3 of the subject and the entrance pupil of the image capture apparatus 10,
  are close to each other, forming an angle θ of less than 15 degrees, or preferably, of less than 5 degrees, or even more preferably of less than 1 degree.

Having such a gaze direction $z_G$, that is close to the observation direction $z_o$, is preferable as it enables to determine a refraction error of the eye 3 that is close to the central vision refraction error of this eye 3.

The observation direction $z_o$ is the direction presented, just in front of the eye 3, by the mean optical path that links the pupil 30 of the eye 3 to the entrance pupil E10 of the image-capture apparatus 10. In the first embodiment of the portable electronic device 1, in which no additional optical component is interposed between the eye 3 and the image-capture apparatus 10, the observation direction $z_o$ is the direction of the line that passes trough the center of the pupil 30 of the eye 3, and through the center O of the entrance pupil E10 of the image-capture apparatus 10 (FIG. 2). In the second embodiment of the portable electronic device 1', the observation direction $z_o$ is the direction in which the image-capture apparatus 10 is optically, visually located, viewed from said eye 3.

Preferably, the above-mentioned message invites the subject to look at said visual target 6, this visual target 6 being located in a direction close to the observation direction $z_o$ and far away from the subject. So, during the acquisition, or acquisitions of the pictures of the eye 3 of the subject, this eye 3 is focused on said visual target 6 located far away from him. This makes the determination of the above-mentioned refraction features of this eye 3, carried on at step c), easier and more accurate.

During step S'o, the subject is also incited to reduce ambient light intensity as much as possible, and/or to go to a place with low ambient light intensity.

The steps a) and b) are now described in detail.

As already mentioned, in step a), a lighted area is displayed on the screen 11 of the portable electronic device 1; 1', to form a light source 12A, 12B, 12C (FIGS. 2 and 4A to 4C). During this step, the main part of the rest of the screen 11, particularly the surrounding of the lighted area, is dark and emits no light, or at least emits a light whose intensity is negligible compared to the one emitted by said lighted area.

The light source preferably illuminates the pupil of the eye by a flash of light, that is by a brief pulse of light, rather than illuminating it continuously. Indeed, a photorefraction measurement is all the more precise than the pupil 30 of the eye 3 is dilated, and with a brief or intermittent illumination of this pupil, contraction/closure of the pupil can be avoided, or at least is smaller than with a continuous illumination. The duration of this flash of light, defined for instance as this pulse of light full temporal width at half-maximum, is preferably smaller than 0.1 second, or even smaller than 0.03 seconds. If the emission of this flash of light is periodically repeated with a given period, the ratio of this flash duration to said period is preferably smaller than 10 percent (10%).

To prevent contraction/closure of the illuminated pupil 30, the screen 11 is also controlled so that the lighted area displayed on the screen 11 emits a limited amount of blue light. Indeed, blue light is known to provoke pupil contraction/closure.

For instance, a ratio equal to:
the intensity of blue light emitted by the lighted area, that is the intensity of the light emitted by the lighted area within the wavelength range comprised between 400 nanometers and 520 nanometers, divided by
the total intensity of the light emitted by this lighted area is maintained below ten percent (10%).

For instance, when the screen 11 is an LCD screen with red, green, and blue pixels, blue pixels are turned off during steps a) and b).

The image-capture apparatus 10 and the screen 11 operations are synchronized, so that the picture, or the pictures acquired at step b) are acquired while the pupil 30 of the eye is being illuminated by the lighted area displayed on the screen 11.

Particularly, when the pupil 30 is illuminated by means of the above-mentioned flash of light, the image-capture apparatus 10 is controlled so that the time lapse during which the picture of the eye 3 is acquired, that is, the integration time, encompasses the time lapse during which said flash of light is emitted.

In the exemplary embodiment of the method described here, in step a), the lighted area provides a time-varying illumination, that varies periodically in time with a given modulation frequency F. For instance, the emission of the above-mentioned flash of light is repeated at this modulation frequency F.

In step b), a plurality of pictures of the pupil 30 of the eye 3 of the subject 2 is then acquired, in a synchronized manner with said time-varying illumination.

This feature enables a time/frequency filtering of the sequence of images of the retinal reflection 31 thus acquired, in order to recover a component of said sequence having said modulation frequency.

The modulation frequency F is preferably different from power supply frequencies. Noise components varying at the power supply frequencies, generally equal to 50 hertz, 60 hertz, or to an integer number times one of these base frequencies, can thus be removed from said sequence of images, thanks to the above-mentioned time/frequency filtering. As an example, the modulation frequency F may be comprised between 5 and 30 hertz, which leads to a good rejection of the noise components at the power supply frequencies.

The group of steps comprising step a) and step b) can be executed one time only. However, in the exemplary embodiment of the method described here, this group of steps is executed several times successively, as represented on FIG. 1, in order to acquire a plurality of pictures of the pupil 30 of the eye 3 of the subject 2, comprising an image of the retinal reflection 31, for a respective plurality of postures of the head 4 of the subject 2 relative to said light source 12A, 12B, 12C, that is to say for a respective plurality of positions and/or orientations of the light source, relative to the head 4 of the subject 2.

Here, more specifically, the group of steps comprising step a) and step b) is executed several times successively in order (FIG. 5):
to acquire a plurality of pictures of the eye, for a respective plurality of values of the light source eccentricity, and
to acquire a plurality of pictures of the eye 3, for a respective plurality of measurement axis $x_o$, $x_P$, $x_Q$, having different respective orientations relative to the face/eye of the subject 2, so that astigmatism features of the eye 3 can be determined.

Figure 4B:
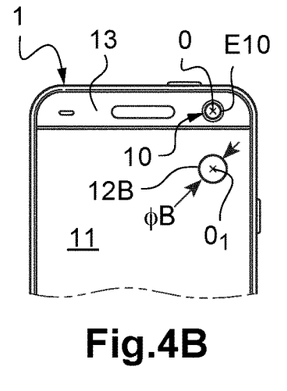
Figure 4C:
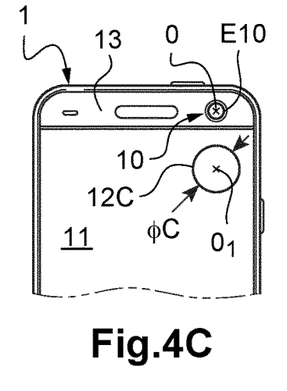

In addition, this group of steps is also executed several times successively, for various sizes of the lighted area forming said light source 12A, 12B, 12C (as represented on FIGS. 4A to 4C).

During a first set of successive executions of the group of steps comprising steps a) and b), the position of the lighted area 12A displayed on the screen 11 is varied, from one execution to the other. During this plurality of executions of step a), the lighted area 12A is thus centered successively on a respective plurality of distinct positions O1, O2, O3, . . . , on the screen 11, as represented on FIG. 5. These positions are positions defined relatively to the screen 11 of the portable electronic device 1; 1'.

The lighted area 12A is thus centered successively at a plurality of distinct, predetermined offset distances $d_{o,1}$, $d_{o,2}$, $d_{o,3}$, . . . from the center O of the entrance pupil E10 of the image-capture apparatus 10.

The eccentricity e between the light source 12A and the entrance pupil E10 of the image capture apparatus 10 is thus varied from one execution of step a), to the other.

Realizing such an ensemble of measurements, for a plurality of values of the eccentricity, leads to an improved accuracy of the refractive features finally determined at step c).

The various positions O1, O2, O3, . . . , on which the lighted area 12A is successively centered, are located along the first measurement axis $x_o$, stationary with respect to the portable electronic device 1; 1', and that passes through the center O of the entrance pupil E10 of the image-capture apparatus.

During this first set of successive executions of steps a) and b), the portable electronic device 1; 1' is held stationary with respect to the subject 2. Thus, the relative position and orientation of the image-capture apparatus 10 and the eye 3 of the subject 2 remains the same. The relative orientation of the screen 11 and the eye 3 of the subject 2 remains also the same. Thus, the orientation of the first measurement axis $x_o$ relative to the eye 3 and face 4 of the subject 2 remains the same during this first set of repetitions of the illumination and acquisition steps a) and b).

Preferably, the method comprises a second set of successive executions of the illumination and acquisition steps a) and b), identical to the first set described above except from the fact that the positions P1, P2, P3, . . . , on which the lighted area 12A is successively centered during this second set, are located along a second measurement axis $x_P$, distinct from the first measurement axis $x_O$ (FIG. 5).

As explained above in the section relative to the principle of eccentric photorefraction, realizing such measurements for two, or even three distinct measurement axis $x_O$, $x_P$, enable to determine astigmatism features of the eye 3 of the subject.

For this determination to be as accurate as possible, the angle between the second measurement axis $x_P$ and the first measurement axis $x_O$ is preferably comprised between 60 and 120 degrees. The second axis also passes through the center O of the entrance pupil E10 of the image-capture apparatus 10.

The method may also comprise a third set of successive executions of the illumination and acquisition steps a) and b), during which the position of the lighted area 12A displayed on the screen 11 is varied, from one execution to the other, along a third measurement axis $x_Q$, distinct from the first and second measurement axis $x_O$ and $x_P$ (FIG. 5). This third axis also passes through the center O of the entrance pupil E10 of the image-capture apparatus 10. The angle between this axis and the first axis is preferably comprised between 30 and 60 degrees.

In the exemplary embodiment of the method described here, the portable electronic device 1; 1' is held stationary, with respect to the eye 3 and face 4 of the subject 2, all along the first, second and third set of executions of steps a) and b).

However, alternatively, and in a case in which the method is implemented by the portable electronic device 1 according to the first embodiment (FIG. 2), the orientation of the electronic device 1, relative to the subject's head 4, could be varied from a set of acquisitions to the other, in order to modify the orientation of the measurement axis. In this case, the lighted area 12A is displayed at the same successive positions O1, O2, O3 on the screen, regardless of the set of executions considered, and the modification of the orientation of the measurement axis is obtained by rotating the portable electronic device 1, around an axis roughly parallel to the observation axis $z_o$.

Alternatively, steps a) and b) could also be executed one time only for each measurement axis $x_O$, $x_P$, $x_Q$, instead of being executed several times for each of these measurement axis. In this case, the lighted area 12A remains centered at a same predetermined offset distances $d_{o,1}$ from the center O of the entrance pupil E10 of the image-capture apparatus 10, from one acquisition to the other.

In another variant, in a case in which the method is implemented by the portable electronic device 1 according to the first embodiment (FIG. 2), steps a) and b) are repeated in order to capture a plurality of pictures of the eye 3, and in each of the repeated steps a), the relative position of the image-capture apparatus 10 and the eye 3 of the subject is modified, while the lighted area 12A remains centered at a same predetermined distance $d_{o,1}$ from the center O of the entrance pupil E10 of the image-capture apparatus 10. In this variant, more specifically, the orientation of the electronic device 1 relative to the subject's head 4 is modified between each execution of step a), by rotating the portable electronic device 1 around an axis roughly parallel to the observation axis $z_o$. The orientation of the measurement axis thus changes from one execution of step a) to the other, while the eccentricity remains the same. As explained above in the section relative to the principle of eccentric photorefraction, this enables to determine astigmatism features of the eye 3.

The method can also comprise a fourth set of successive executions of the illumination and acquisition steps a) and b), during which a dimension, here a diameter of the lighted area, is varied, from one execution to the other. During this plurality of executions of step a), the lighted area 12A, 12B, 12C thus presents successively a respective plurality of different diameters $\phi_A$, $\phi_B$, $\phi_C$ (FIGS. 4A to 4C). These various diameters can be comprised between 1 and 15 millimeters.

For a bigger diameter of the lighted area, the total amount of light available to illuminate the retina of the eye 3 is higher, but, in return, the light source thus formed is less punctual. Thanks to this fourth set of acquisitions, pictures of the eye 3 acquired for various conditions of illuminations are available. This enables to select, a posteriori, among these pictures, those acquired under the illumination conditions the most appropriate to the subject 2 and to environment where these acquisitions are carried on.

Anyhow, illuminating the retina of the eye 3 by displaying a wide lighted area on the screen 11, like lighted area 12C, for instance a 10 millimeters-wide area, permits to illuminate said retina with a higher intensity than with a punctual-like light source, which is valuable when the environment of subject is not completely dark.

In the exemplary embodiment of the method described here, after some or all the executions of step b), the picture or one of the pictures acquired in step b) is displayed on the screen 11 of the portable electronic device 1; 1', as a kind of feed-back picture. The subject 2 can thus check that step b) was successful, which means that the acquired picture actually comprises, clearly distinguishable, the image of the retinal reflection 31. A message can also be displayed on the screen, inviting the subject 2 to confirm that step b) was successful, steps a) and b) being otherwise executed again.

Steps a') and b')

The method comprises here, next to steps a) and b), the following steps (FIG. 1):

a') illuminating said pupil 30 of the eye 3 of the subject 2 by displaying an extended lighted area on the screen 11 of the portable electronic device 1; 1', said extended lighted area filling at least one tenth, preferably one third of the overall area of said screen, and b') acquiring a picture of said pupil 30 of the eye 3 of the subject 2, by means of the image-capture apparatus 10 of the portable electronic device 1; 1'.

This extended lighted area is large enough so that, in the image acquired in step b'), the reflection, on the retina of the eye 3, of the light emitted by the extended lighted area, fulfills the entire pupil 30 of the eye.

So, the image of this pupil 30 can be precisely identified and delineated, in the picture acquired in step b'), leading to an accurate determination of the diameter r of the pupil 30.

Alternatively, steps a') and b') could be omitted, the pupil 30 diameter being then determined, in step c), by processing the picture or pictures acquired in step b).

Step c)

It is recalled that, in the exemplary embodiment described here, during the executions of steps a) and b), the lighted area spot provides a time variable illumination with said modulation frequency F, and that a sequence comprising a plurality of images of the retinal reflection 31 is captured in step a).

Step c) then comprises a step of filtering the images of said sequence to extract the component of this sequence varying at the modulation frequency F.

This filtering can be achieved by synchronous demodulation, for instance. It could also be achieved by selecting, among said images, those acquired while the flash of light illuminating the eye 3 of the subject was on, and discarding the other images, subtracting from said image an image acquired while the flash of light was off, to obtain a corrected image and then by calculating a filtered image by averaging together these corrected images, by calculating their sum, for instance.

Alternatively, such a time and/or frequency filtering could be applied to a sequence of quantities, such as the retinal reflection size s, determined from this sequence of images, instead of being applied directly to the sequence of acquired images itself.

Anyhow, for each of the preceding executions of steps a) and b), a value of the size $\underline{s}$ and a value of the tilt angle of the retinal reflection 31 are determined, by image analysis, from the picture acquired in step b), or from the component of said sequence of images extracted by filtering. For example, the size $\underline{s}$ is obtained by multiplying the dimension $\underline{s}_I$ of the image of this reflection 31, measured in said picture and expressed as a number of pixels, by the conversion coefficient C determined in the calibration step So.

Thanks to the repetitions of steps a) and b), carried on for different values of the eccentricity e, and for several measurement axis $x_o$, $x_P$, $x_Q$ having different orientations, a set of several corresponding values of the size $\underline{s}$ and of the tilt angle of the retinal reflection 31 are determined in step c).

Refractive features of the eye 3, comprising here the spherical power and the cylindrical power of the refraction error of the eye 3, and the orientation of the axis of the corresponding cylinder, are then determined from:
- this set of values of the sizes and of the tilt angle of the retinal reflection 31,
- the corresponding values of the eccentricity e of the light source, and the corresponding orientations of the measurement axis $x_o$, $x_P$, $x_Q$ with respect to the eye 3 of the subject 2,
- the optical distance d between the pupil 30 of the eye 3 and the entrance pupil E10 of the image-capture apparatus 10, determined here during the calibration step So, and
- a value of the diameter r of the pupil 30, determined from the picture of the eye 3 acquired in step b').

The determination of these refractive features is carried on according to the eccentric photorefraction method, whose principle has been recalled above.

It is noted that, in the case in which the method is executed by the portable electronic device 1 according to the first embodiment, the eccentricity e is determined as the smallest distance, e1, between the entrance pupil E10 of the image-capture apparatus 10 and the light source 12A, 12B, 12C, as mentioned above.

In the case in which the method is executed by the portable electronic device 1' according to the second embodiment, the eccentricity e is determined quite similarly, by considering the virtual image of the portable electronic device 1' projected in front of the subject 2 by the additional optics 30', 34'. This virtual image comprises an image of the entrance pupil of the image-capture apparatus 10, and an image of said light source. In this case, the eccentricity e is determined as the smallest distance, e1', between said image of the entrance pupil of the image-capture apparatus 10, and said image of the light source.

The orientations of the measurement axis $x_o$, $x_P$, $x_Q$, with respect to the eye 3 of the subject 2, can be determined on the basis of an orientation of the portable electronic device 1; 1' relative to the head 4 or the eye 3 of the subject 2, this last orientation being determined by mean of a numerical analysis of one of the captured picture.

Alternatively, the orientations of the measurement axis $x_o$, $x_P$, $x_Q$, with respect to the eye 3 of the subject 2, could be determined on the basis of an orientation of the portable electronic device 1 relative to the vertical determined on the basis of data acquired by the inertial unit of the portable electronic device 1 in step b), while the corresponding picture or pictures were acquired.

Taking into account a set of several values of the sizes of the retinal reflection 31, each corresponding to a different value of the eccentricity e, improves the accuracy of the refractive features thus determined, compared to a case in which the eccentricity would remain the same for all the pictures acquired. These refractive features can be determined, for example, by a curve fitting process, taking this set of values of the size s, and the corresponding values of the eccentricity e as input data.

If the picture, or pictures, are acquired while the subject 2 wears a corrective ophthalmic lens in front of his eye 3, or in contact with his eye 3, at step b), then, the refractive feature or features of this lens are taken into account while determining the refractive features of his eye 3. For example, if a contact lens is present on the eye 3 of the subject, the spherical power of this lens is added to the spherical power, determined as explained above from the sizes of the corneal reflection 31.

If the subject 2 was invited to look at the image-capture apparatus 10, or to look at the light source 12A, 12B, 12C, at step S'$_o$, it is considered that the eye 3 of the subject was focused on the image-capture apparatus 10, or on light source 12A, 12B, 12C respectively, during the pictures acquisitions. In the process of determining said refractive features, the portable electronic device 1; 1' then takes into account that the eye 3 of the subject was focused on, that is to say was accommodating on an object located at a finite distance, more specifically located at said optical distance d, during the acquisitions of the pictures of this eye 3. To the end, suitable corrections are applied to the refractive features of the eye 3 deduced form the size $\underline{s}$ of the retinal reflection 31. For instance, if the optical distance d is equal to 1 meter, and if the spherical power determined from the size of the retinal reflection s is equal to −2 diopters, then, the value of spherical power finally determined and delivered by the portable electronic device 1; 1' is equal to −3 diopters.

If the subject 2 was invited, at step S'o, to look at the visual target 6 located several meters ahead of him, the portable electronic device 1; 1' may determine said refractive features while considering that the eye 3 of the subject was focused on an object located infinitely far away, during the acquisitions of said pictures. In this case, the above-mentioned corrections may be omitted.

The method may also comprise a step of transmitting the refraction features of the eye 3 of the subject 2, determined in step c), to a remote data server, by means of the communication module of the portable electronic device 1; 1'.

The method may also comprise a step of proposing to the subject 2 to order an optical equipment from a remote, online supplier, the characteristics of this optical equipment being preselected automatically, that is, without requesting an action from the subject 2, on the basis of refraction features determined in step c). These characteristics may comprise the spherical and/or cylindrical power of the corrective ophthalmic lens or lenses of this optical equipment. During this step, this optical equipment is ordered by means of the communication module of the portable electronic device 1; 1'.

Lighting Conditions Management

Illuminating the pupil 30 of the eye 3 by means of a lighted area displayed on the screen 11 of the portable electronic device 1; 1' provides several advantages and a lot of flexibility, as explained above.

Though, depending on the particular portable electronic device considered, the brightness of the light source formed by this lighted area could be rather small, compared to the brightness of the light source of a conventional retinoscope. It is though preferable to carry on this method in a dark or very dimly lighted environment E.

So, in the embodiment described here, the method comprises a group of steps that enables to check that the lighting conditions in the environment E are adequate to determine the refractive features of the eye 3 of the subject 2, in particular that an ambient light intensity is small enough. More specifically, the method comprises here the steps of:
  measuring the ambient light intensity $I_A$ and/or an intensity, $I_R$, of the reflection 31 of the light source 12A, 12B, 12C on the retina of the eye 3 of the subject,
  determining a lighting conditions parameter that takes into account the measured ambient light intensity $I_A$ and/or the measured intensity of said reflection, $I_R$,
  comparing said parameter with a predetermined threshold, and
  depending on the result of this comparison, determining:
    that the determination of refractive features or feature of the eye 3 of the subject is feasible and/or reliable,
    or, on the contrary,
      that the determination of these refractive features or feature is not feasible or reliable, and that the ambient light intensity $I_A$ should be reduced.

The ambient light intensity $I_A$ can be measured directly, by means of a dedicated sensor, like a photodiode or a camera, distinct from the image-capture apparatus 10.

It could also be measured indirectly, by processing one or several of the pictures acquired at step b), or b'). In this case, the ambient light intensity $I_A$ can be determined as being equal to, or representative of an average brightness level of the pixels of said picture, or of the pixels of a given region of said picture.

Here, the intensity of the reflection 31, $I_R$, is measured indirectly, by processing one or several of the pictures acquired at step b). This intensity is representative of an average brightness level of the pixels of the image of said reflection 31, for example.

The lighting conditions parameter that is then determined is representative of the feasibility of the determination of the refractive features of the eye 3 of the subject, under the lighting conditions in the subject's environment E.

The lighting conditions parameter can be determined as being representative of the ambient light intensity $I_A$ divided by the intensity of said reflection $I_R$. For example, it can be equal to this ratio $I_A/I_R$, which is a kind of signal to noise ratio.

Alternatively, the lighting conditions parameter could be determined as being representative of the ambient light intensity $I_A$ alone, or as being representative of the inverse $1/I_R$ of the intensity of said reflection, $I_R$.

When the lighting conditions parameter is found to be smaller than the predetermined threshold, the portable electronic device determines that the determination of refractive features or feature of the eye 3 of the subject is feasible and/or reliable.

This predetermined threshold may be equal to the value of said lighting conditions parameter in a threshold situation in which the intensity of the ambient light incident on the subject's face is equal to 1000 candela per square meter, or preferably equal to 300 candela per square meter, or even more preferably, to 50 candela per square meter.

Otherwise, the portable electronic device determines that the determination of refractive features or feature of the eye 3 is not feasible or reliable, and that the ambient light intensity $I_A$ should be reduced. In this case a message can be displayed on the screen 11, or emitted as an audible message, inviting the subject to reduce the ambient light intensity.

It is noted that, in the method according to the invention, the refraction features of the eye 3 of the subject 2 can also be determined on the basis of one or more intensity profiles of the retinal reflection 31, as already mentioned. In this case, steps So, So', a), b), a'), b') and c) can be executed in a way similar to the one described above, with slight modifications, however, compared to the case of a determination based on the size of reflection 31. However, in this case, the method does not comprise the fourth set of successive executions of steps a) and b) described above, during which the size of the light source varies.

The method for determining one or more refraction features of the eye 3 of the subject 2, that has been presented above can be applied to the determination of the refraction feature or features of each of the two eyes of the subject 2.

In other embodiments of the method, in which the method is implemented by means of the first embodiment of portable electronic device 1, the screen 11 and image-capture apparatus 10 of this device 1 could be directed to a mirror. In this case, the subject looks at the portable electronic device 1 through this mirror. The optical distance, between the eye 3 of the subject and the point he is looking at, is thus increased. The eye 3 of the subject is thus focused on a point that is optically farthest than if the subject 2 would look directly at the portable electronic device, without said mirror, which increases the accuracy of the determination of the refractive feature or features of this eye 3.

The invention claimed is:

1. A method for determining a refraction feature of an eye of a subject using a portable electronic device, said portable electronic device including:
  a light source adapted to illuminate a pupil of said eye of the subject; and
  an image-capture apparatus adapted to acquire pictures of said pupil illuminated by said light source,
  said method comprising the steps of:
  a) illuminating said pupil of the eye of the subject by means of said light source;
  b) acquiring a picture of said pupil of the eye of the subject comprising an image of the reflection of said light source on the retina of said eye of the subject;
  c) determining said refraction feature of said eye of the subject taking into account at least one of the following features of said image of the reflection of said light source:
    a geometrical feature of said image of the reflection of said light source,
    a positional feature of said image of the reflection of said light source, an intensity distribution within said image of the reflection of said light source;
wherein said portable electronic device being held by the subject himself in front of his eyes,
said step a) comprises displaying, on a screen of said portable electronic device, a lighted area forming said light source, and
in step b) said reflection of said light source is collected by said image-capture apparatus,
wherein a plurality of pictures of said pupil of the eye of the subject comprising an image of the reflection of said light source on the retina of said eye of the subject are acquired,
wherein the posture of the head of the subject relative to said light source is different while each of said pictures are acquired, and in step c), said refraction feature is determined taking into account at least a geometrical feature and/or a positional feature and/or an intensity distribution of each of the images of the reflection of said light source on each picture acquired, and
wherein steps a) and b) are repeated in order to capture said plurality of pictures, and
in each of the repeated steps a), the lighted area is centered at a different predetermined distance from the center of the entrance pupil of the image-capture apparatus, the relative position of the image-capture apparatus and the eye of the subject remaining the same,
in each of the repeated steps b), the picture of the pupil of the eye of the subject is acquired while the picture comprises the image of the reflection of said lighted area centered at said different predetermined distance from the center of the entrance pupil of the image-capture apparatus.

2. The method according to claim 1, comprising a step of modifying the position and/or the orientation and/or dimension of the light source between the acquisition of two different pictures of said plurality of pictures.

3. The method according to claim 2, wherein said position and/or orientation and/or dimension is modified between two acquisitions of a picture by modifying the position and/or dimension of the lighted area displayed on said screen and/or by modifying the relative position and/or orientation of the portable electronic device and the head of the subject.

4. The method according to claim 1, further comprising a step of determining an optical distance between the entrance pupil of the image-capture apparatus and the pupil of the eye of the subject by scaling a picture of the eye or head of the subject acquired by said image-captured apparatus and wherein, in step c), said optical distance is taken into account for determining said refraction feature.

5. The method according to claim 4, wherein said picture of the eye or head of the subject is scaled by identifying, on the picture, the images of two remarkable points of the head of the subject or by identifying an image of a predetermined object held close of the head of the subject during step b).

6. The method according to claim 1, further comprising the steps of:
acquiring data relative to a position of the electronic device in space, by means of a position determination module embedded in the electronic device, and
determining a relative position of the electronic device and the head of the subject taking into account this data.

7. The method according to claim 1, wherein, in step a), said light source illuminates the pupil of the eye by a flash of light and the image-capture apparatus is synchronized to capture an image simultaneously, while the eye is illuminated by this flash of light.

8. The method according to claim 1, wherein, in step a), said lighted area emits a limited amount of blue light.

9. The method according to claim 1, wherein, in step a), said lighted area provides a time variable illumination with a time frequency different from power supply frequencies, in step b), a sequence comprising a plurality of images of said reflection is captured, and, in step c), a step of filtering the images of said sequence to recover a component of said sequence having said time frequency is performed.

10. The method according to claim 1, further comprising the steps of:
measuring an ambient light intensity and/or an intensity of said reflection, on the retina of the eye of the subject, of the light emitted by said light source,
determining a lighting conditions parameter taking into account said measured ambient light intensity and/or said measured intensity of said reflection, and
comparing said parameter with a predetermined threshold.

11. The method according to claim 1, wherein:
in step a), the light emitted by the said source illuminates the pupil of the eye of the subject directly, without interacting with any other optical component of said portable electronic device; and wherein
in step b), the reflection of said light source on the retina of said eye is collected directly by said image-capture apparatus, without interacting with any other optical component of said portable electronic device.

12. A portable electronic device comprising:
a light source adapted to illuminate a pupil of an eye of a subject;
an image-capture apparatus adapted to acquire pictures of said pupil illuminated by said light source, and
a control unit programmed to execute the steps of:
a) illuminating said pupil of the eye of the subject by means of said light source;
b) acquiring a picture of said pupil of the eye of the subject comprising an image of the reflection of said light source on the retina of said eye of the subject;
c) determining said refraction feature of said eye of the subject taking into account at least one of the following features of said image of the reflection of said light source:
a geometrical feature of said image of the reflection of said light source,
a positional feature of said image of the reflection of said light source,
an intensity distribution within said image of the reflection of said light source;
wherein the control unit is programmed so that, said portable electronic device being held by the subject himself in front of his eyes:
said step a) comprises displaying, on a screen of said portable electronic device, a lighted area forming said light source, and
in step b) said reflection of said light source is collected by said image-capture apparatus,
the posture of the head of the subject relative to said light source is different while each of said pictures are acquired, and in step c), said refraction feature is determined taking into account at least a geometrical feature (s) and/or a positional feature and/or an intensity distribution of each of the images of the reflection of said light source on each picture acquired, steps a) and b) are repeated in order to capture said plurality of pictures, and in each of the repeated steps a), the lighted area is centered at a different predetermined distance from the center of the entrance pupil of the image-capture apparatus, the relative position of the image-capture apparatus and the eye of the subject remaining the same, in each of the repeated steps b), the picture of the pupil of the eye of the subject is acquired while the picture comprises the image of the reflection of said lighted area centered at said different predetermined distance from the center of the entrance pupil of the image-capture apparatus.

* * * * *